United States Patent
Gysling et al.

(10) Patent No.: US 6,435,030 B1
(45) Date of Patent: Aug. 20, 2002

(54) MEASUREMENT OF PROPAGATING ACOUSTIC WAVES IN COMPLIANT PIPES

(75) Inventors: Daniel L. Gysling, Glastonbury; Rebecca S. McGuinn, Middletown, both of CT (US)

(73) Assignee: Weatherford/Lamb, Inc., Houston, TX (US)

(*) Notice: Subject to any disclaimer, the term of this patent is extended or adjusted under 35 U.S.C. 154(b) by 0 days.

(21) Appl. No.: 09/344,070

(22) Filed: Jun. 25, 1999

(51) Int. Cl.[7] .............................................. G01N 29/00
(52) U.S. Cl. ......................... 73/587; 73/589; 73/861.27
(58) Field of Search ...................... 73/570, 597, 861.27, 73/861.28, 602, 587, 608, 589

(56) References Cited

U.S. PATENT DOCUMENTS

| | | | |
|---|---|---|---|
| 4,080,837 A | 3/1978 | Alexander et al. ............ 73/61.1 |
| 4,144,768 A | 3/1979 | Andersson et al. ............ 73/646 |
| 4,159,646 A | * 7/1979 | Paulsen et al. ................ 73/194 |
| 4,164,865 A | * 8/1979 | Hall et al. ...................... 73/194 |
| 4,236,406 A | * 12/1980 | Reed et al. ..................... 73/61.1 |
| 4,445,389 A | 5/1984 | Potzick et al. ............. 73/861.27 |
| 4,520,320 A | 5/1985 | Potzick et al. ............... 328/133 |
| 5,040,415 A | 8/1991 | Barkhoudarian ............. 73/198 |
| 5,083,452 A | 1/1992 | Hope ......................... 73/61 R |
| 5,207,107 A | * 5/1993 | Wolf et al. ............... 73/861.04 |
| 5,218,197 A | 6/1993 | Carroll .................. 250/227.19 |
| 5,363,342 A | 11/1994 | Layton et al. ............... 367/149 |
| 5,398,542 A | 3/1995 | Vasbinder .................... 73/40.5 |
| 5,591,922 A | 1/1997 | Segeral et al. ........... 73/861.04 |
| 5,639,667 A | 6/1997 | Heslot et al. ................ 436/148 |
| 5,741,980 A | 4/1998 | Hill et al. ................. 73/861.04 |
| 5,842,347 A | 12/1998 | Kinder ........................ 62/49.2 |
| 5,845,033 A | 12/1998 | Berthold et al. .............. 385/12 |
| 5,925,821 A | * 7/1999 | Bousquet ..................... 73/592 |

FOREIGN PATENT DOCUMENTS

DE  195 11 234  12/1995

OTHER PUBLICATIONS

"Noise and Vibration Control Engineering Principles and Applications", Leo L. Beranek and Istvan L. Ver, A Wiley Interscience Publication, pp. 537–541.

* cited by examiner

*Primary Examiner*—Hezron Williams
*Assistant Examiner*—Jacques Saint-Surin
(74) *Attorney, Agent, or Firm*—Howrey, Simon, Arnold & White, LLP

(57) ABSTRACT

A pipe 16 having a produced fluid 18 (liquid an/or gas) and at least two acoustic pressure sensors 20–24, is provided with a cylindrical sleeve 30 attached to the pipe 16 at two locations around a sensing region where the sensors 20–24 are located, the sleeve forming a closed cavity 32 filled with a fluid (or material) having an acoustic impedance ($\rho c2$) that is much less than the acoustic impedance ($\rho c1$) of the produced fluid 18 in the pipe 16 (i.e., $\rho c2 \ll \rho c1$), which causes the sleeve 20 to isolate the acoustic sensors 20,22,24 from being affected by acoustic properties of the cavity 32 and the acoustic properties outside the pipe 16. For most effective acoustic, the cavity 32 may be evacuated.

22 Claims, 5 Drawing Sheets

MEASUREMENT OF PROPAGATING ACOUSTIC WAVES IN COMPLIANT PIPES

CROSS REFERENCES TO RELATED APPLICATIONS

Commonly owned, co-pending U.S. patent applications, Ser. No. 09/344,094, entitled "Fluid Parameter Measurement in Pipes Using Acoustic Pressures", filed contemporaneously herewith, contains subject matter related to that disclosed herein.

TECHNICAL FIELD

This invention relates to the measurement of acoustic waves and more particularly to measurement of acoustic waves in pipes.

BACKGROUND ART

It is known that the speed of sound $a_{mix}$ of fluids in pipes may be used to determine various parameters of the fluid. It is also known to use ultrasonic acoustic signals as the sound signal measured, to determine the speed of sound. Ultrasonic signals are high frequency, short wavelength signals (i.e., wavelengths that are short compared to the diameter of the pipe). Typical ultrasonic devices operate near 200 kHz, which corresponds to a wavelength of about 0.3 inches in water. Some examples of ultrasonic meters are described in U.S. Pat. No. 4,080,837, entitled "Sonic Measurement of Flow Rate and Water Content of Oil-Water Streams", to Alexander et al., U.S. Pat. No. 5,115,670, entitled "Measurement of Fluid Properties of Two-Phase Fluids Using an Ultrasonic Meter", to Shen, and U.S. Pat. No. 4,114,439, entitled "Apparatus for Ultrasonically Measuring Physical Parameters of Flowing Media", to Fick.

The advantage of using wavelengths that are short compared to the diameter of the pipe, is that the fluid behavior approaches that of a fluid in an unbounded media. In an unbounded, homogeneous multi-component mixture, the speed of sound can be expressed as a purely a function of the properties of the components and volumetric phase fractions. In that case, the sound speed is also wavelength (or frequency) independent.

However, as longer wavelengths are used (below the ultrasonic range), the acoustic behavior at the fluid begins to interact with the pipe and surrounding media. The influence of these the boundary effects can fundamentally alter the propagation of sound within the fluid. These effects tend to be wavelength dependant. The propagation velocity (or sound speed) in a bounded system becomes the property of the fluids and the rest of the system with which the fluid interacts. The boundary effects manifest themselves as uncertainty in both measuring and interpreting the sound speed in terms of fluid properties. This uncertainty introduced by the rest of the system diminishes the ability to interpret sound speed measurements. For example, in an oil well, a inner production tube is acoustically coupled to the entire formation and such coupling is dependent on the properties of the produced fluid, the production tubing, the annulus fluid, the casing and the formation.

Furthermore, the associated boundary effects of such coupling introduce dispersion to the propagation of sound within the produced fluid, thereby making the propagation velocity wavelength (and frequency) dependent. This effect is increased as the compliance of the pipe increases.

SUMMARY OF THE INVENTION

Objects of the present invention include provision of a system for measuring the acoustic waves in pipes which is not significantly affected by external system characteristics.

According to the present invention, a pipe having at least two acoustic sensors that sense acoustic pressures of a produced fluid in a pipe along a sensing section, comprises: an outer sleeve, attached to the pipe at two attachment locations along the pipe, said sleeve forming a cavity between said sleeve and said pipe in the sensing section.

According further to the present invention, said cavity is filled with a cavity material having an acoustic impedance ($\rho c2$) that is much less than the acoustic impedance ($\rho c1$) of the produced fluid.

According still further to the present invention, the produced fluid is a liquid and said cavity is filled with a gas. According still further to the present invention, the produced fluid is a liquid at a liquid pressure and said cavity is filled with a gas at a gas pressure lower than the liquid pressure of the produced fluid. Still further according to the present invention, said cavity is filled with air and the produced fluid comprises oil. Still further according to the present invention, said cavity is evacuated. According further to the present invention, the pressure sensors measure strain on the pipe.

The present invention provides a significant improvement over the prior art by providing a low impedance acoustic media that isolates the acoustics of the produced fluid and the production tube from the surrounding environment. The present invention enables the measurement of propagating long wavelength (with respect to the pipe diameter) acoustic waves such that it can be interpreted with respect to an infinite domain propagation. Also, it is not critical to the present invention how the speed of sound measurement is made, and the invention may be used with active acoustic sources or passive listening techniques. The present invention provides acoustic isolation that enables well defined propagation characteristics and provides advantages associated with isolating the test section from noise from the environment thereby preventing such noise from influencing the measurement of acoustic properties of the fluid in the production tube in the sensing region. The present invention is applicable to many applications including the oil industry, refining, pipe lines, water industry, nuclear industry, or any other application where the speed of sound of a fluid in a pipe or conduit is desired to be measured.

The foregoing and other objects, features and advantages of the present invention will become more apparent in light of the following detailed description of exemplary embodiments thereof.

BEST MODE FOR CARRYING OUT THE INVENTION

Figure 1:
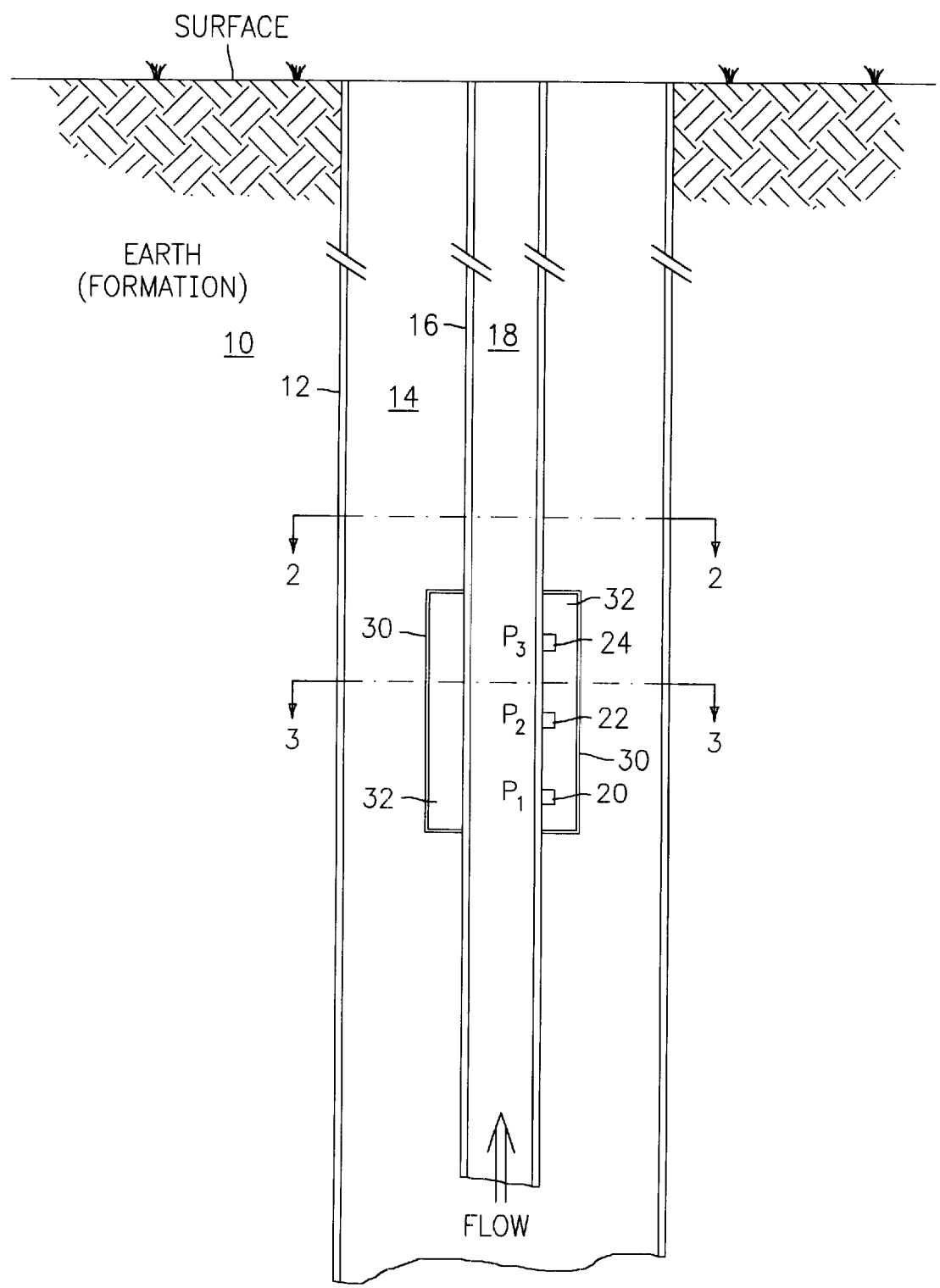
FIG. 1 is a schematic drawing of a series of unsteady pressure sensors in a well, in accordance with the present invention.

Referring to FIG. 1, an oil or gas well is located in a formation 10 having a casing 12 against the formation 10 and a production tubing or pipe 16 located inside the casing 12. Between the casing 12 and the production tubing 16 is an annulus fluid 14 and inside the production tubing 16 is a produced fluid 18, e.g., oil, water or gas mixture. A series of axially spaced acoustic pressure sensors, 20,22,24 located on the pipe 16 measure acoustic (or unsteady or ac or dynamic or time-varying) pressures P1,P2,P3, respectively. The pressures $P_1,P_2,P_3$ may be measured through holes in the pipe 16 ported to the sensors or by measuring the pipe deflection, or microphones, or by other techniques. The pressure sensors 20,22,24 may be similar to those described in copending U.S. patent application, Ser. No. 09/344,094, entitled "Fluid Parameter Measurement in Pipes Using Acoustic Pressures", filed contemporaneously herewith, which is incorporated herein by reference in its entirety.

Figure 3:
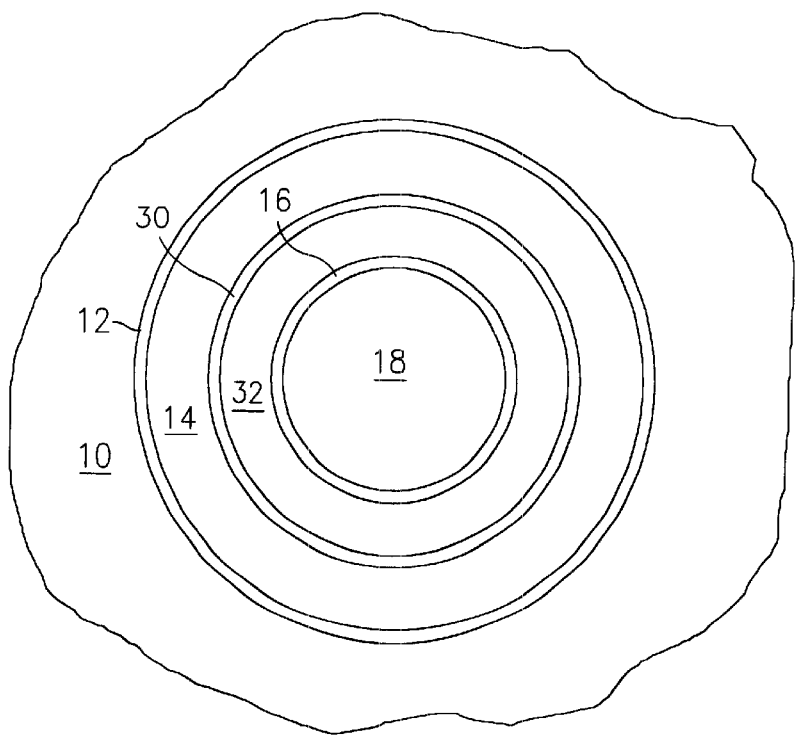
FIG. 3 is a cross section of a portion of FIG. 1 along lines 3—3, in accordance with the present invention.

Referring to FIGS. 1 and 3, an outer cylindrical isolation sleeve 30 (or sheath, shell, housing, or cover) which is attached to the outer surface of production tubing 16 over where the pressure sensors 20,22,24 are located on the pipe 16. The sleeve 30 forms a closed cavity 32 (or chamber) between the pipe 16 and the sleeve 30. The sleeve may have other outer geometries but should circumferentially surround the pipe 16 in the test section, where the sensors 20–24 are located.

We have found that when the cavity 32 is filled with a gas such as air, the speed of sound can be calibrated to the infinite domain (or unbounded media) speed of sound in the produced fluid 18 in the pipe 16. The infinite domain sound speed is the desired property since it is closely linked to the properties of the fluid. In that case, the boundary effects are introduced in a well known and well understood manner such that their effect can be corrected for in the measurement. To provide the most effective isolation, the cavity may be evacuated (i.e., is a vacuum). Alternatively, the cavity 32 may be filled with low impedance gases, such as nitrogen, argon, helium, or other inert gases, or other low impedance gases, provide very effective acoustic isolation. Other gases may be used if desired.

The compliance (or flexibility) of the pipe 16 (or conduit) in the sensing region may influence the accuracy or interpretation of the measured speed of sound of the produced fluid 18 in two ways.

Figure 4:
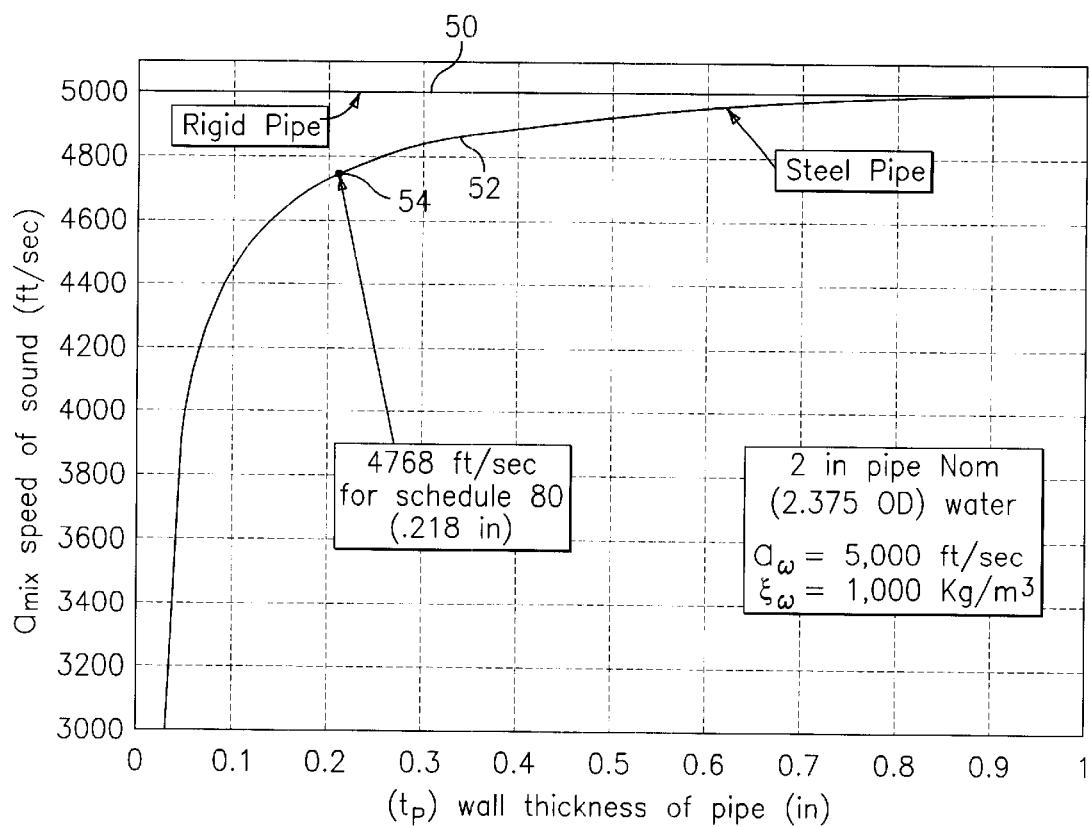
FIG. 4 is a graph showing the speed of sound for a rigid pipe and a non-rigid pipe as a function of pipe wall thickness, in accordance with the present invention.

First, referring to FIG. 4, flexing of the pipe 16 in the sensing region reduces the measured speed of sound $a_{mix}$. In particular, the influence of pipe wall thickness (or compliance of the pipe) on measured speed of sound for a pipe having a 2 inch nominal diameter and having 100% water ($\rho_w$=1,000 kg/m$^3$; $a_w$=5,000 ft/sec) inside the pipe and a vacuum outside the pipe diameter, is shown. The speed of sound of water in an infinitely rigid pipe (i.e., infinite modulus) is indicated by a flat curve 50, and the speed of sound of water in a steel pipe is indicated by a curve 52. A point 54 on the curve 52 indicates the value of the speed of sound of about 4768 ft/sec for a Schedule 80 steel pipe. Accordingly, the thicker the pipe wall, the closer the speed of sound approaches the value of 5,000 ft/sec for an infinitely rigid pipe. The errors (or boundary effects) shown in FIG. 4 introduced by a non-rigid (or compliant) pipe 16 can be calibrated out of the measurement to accurately determine the actual speed of sound in the fluid 18. Thus, in this case, the system does modify the propagation velocity; however, such velocity can be mapped to the propagation velocity in an infinite media in a predictable fashion.

More particularly, for fluids contained in a compliant pipe (or flexible conduit), the propagation velocity of compression waves is influenced by the structural properties of the conduit. For a fluid contained in the pipe 16 surrounded with a fluid of negligible acoustic impedance ($\rho a$), the propagation velocity is related to the infinite fluid domain speed of sound and the structural properties via the following relation:

$$\frac{1}{\rho_{mix} a_{measured}^2} = \frac{1}{\rho_{mix} a_{mix}^2} + \sigma \text{ where } \sigma \equiv \frac{2R}{Et} \qquad \text{Eq. 1}$$

where R=the pipe radius, t is the pipe wall thickness, $\rho$mix is the density of the mixture (or fluid), $a_{mix}$ is the actual speed of sound of the mixture, $a_{measured}$ is the measured speed of sound of the mixture, and E is the Young's modulus for the pipe material. Eq. 1 holds for frequencies where the wavelength of the acoustics is long compared to the diameter of the pipe and for frequencies which are low compared to the natural frequency of the breathing mode of the pipe. This relation is also restricted to wavelengths which are long enough such that hoop stiffness dominates the radial deflections of the pipe. The calibration of the pipe can be derived from other equations or from a variety of other means, such as analytical, experimental, or computational.

Figure 2:
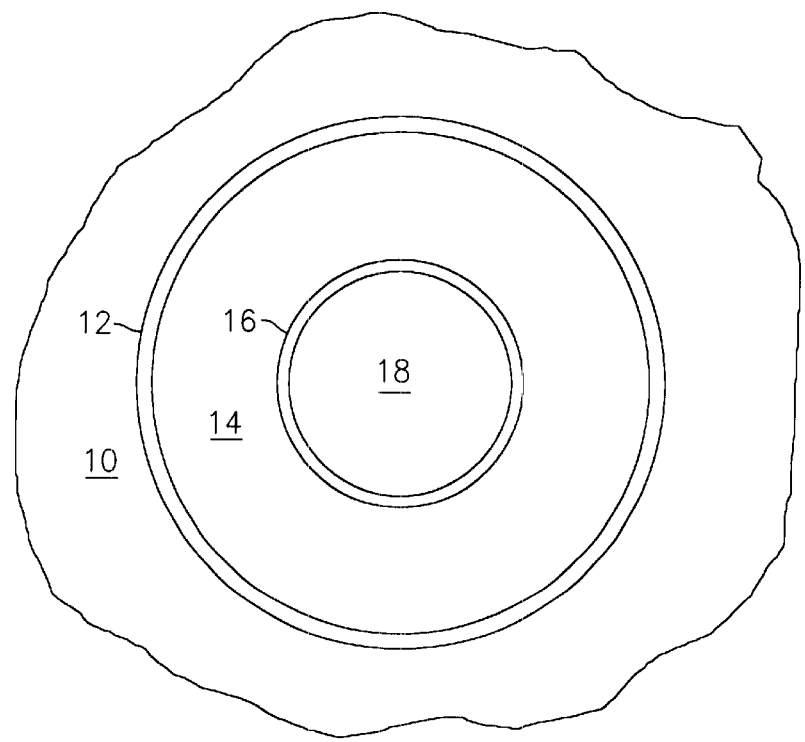
FIG. 2 is a cross section of a portion of FIG. 1 along lines 2—2, in accordance with the present invention.

Second, referring to FIGS. 1 and 2, if the pipe 16 is compliant and acoustically coupled to fluids and materials outside the pipe 16 in the sensing region, it allows the acoustic properties of the fluids and materials outside the pipe 16 diameter, e.g., annulus fluid, casing, rock formations, etc., to influence the measured speed of sound. Because the acoustic properties of such fluids and materials are variable and unknown, their affect on measured speed of sound cannot, in general, be robustly corrected by calibration (nor mapped to the propagation velocity in an infinite media in a predictable fashion).

Also, for high pressure applications where pressure sensors are sensing unsteady pressures in the pipe 16, it may be desirable to reduce the ΔP across the pipe wall to minimize the required wall thickness and to enhance sensitivity of the test section when strain sensing is used. A cylindrical sleeve may be used to accomplish this ΔP reduction by putting a high pressure fluid in the cavity 32. However, this causes the acoustic impedance of the cavity fluid and the produced fluid to become compatible. When the produced fluid is oil, a high pressure oil or water would cause the acoustic impedances to be close enough to cause the aforementioned acoustic coupling.

Referring to FIGS. 1 and 3, for cases where the compliance of the pipe influences the propagation velocity of sound within the pipe by a predetermined amount (e.g., by about 1% or more), we have found that if the acoustic impedance ($\rho c2$) of the material (or fluid) in the cavity 32 is much less than the acoustic impedance ($\rho c1$) of the produced fluid 18 in the pipe 16 (i.e., $\rho c2 < \rho c1$), then the sleeve 20 will serve to isolate the acoustic sensors from being affected by acoustic properties of the cavity or acoustic properties outside the pipe 16. The acceptable ratio between $\rho c2$ and $\rho c1$ depend on the application and the desired sensitivity, pipe thickness, cavity width, sleeve wall thickness, and other related factors. It should be understood that the acoustic impedance $\rho c$ of fluids (liquids and/or gases) varies with pressure, where $\rho$ is the density and c is the speed of sound of the fluid.

The above condition would be satisfied if the produced fluid 18 is a liquid, such as oil and/or water, and the cavity 32 fluid is a gas, such as air, nitrogen, or other gases.

Alternatively, if the produced fluid 18 is a gas (such as methane or another gas in an oil well) contained in a sufficiently compliant pipe such that its propagation velocity is affected by the pipe compliance, then the cavity 32 may also be filled with a different gas (such as air) provided the condition $\rho c2 \ll \rho c1$ described above is still satisfied. However, in general, for produced gas in a steel production pipe, the pipe may not be compliant enough to appreciably influence the propagation of the sound waves within the gas.

We have found that such a low impedance acoustic media isolates the acoustics of the produced fluid 18 and the production tube 16 system from the surrounding environment. The length of the acoustically isolated region 30 should be sufficient to monitor the acoustic propagation, as described in the aforementioned copending patent application. The minimum length is set by the acoustic wavelength of interest, e.g., as a guideline, the length should be at least one half of the wavelength of interest.

The present invention enables the measurement of propagating long wavelength (with respect to the pipe diameter) acoustic waves such that it can be interpreted with respect to an infinite domain propagation.

It should be understood that it is not critical to the present invention how the speed of sound measurement is made, and the invention may be used with active acoustic sources or passive listening techniques. The present invention provides acoustic isolation that enables well defined propagation characteristics and provides advantages associated with isolating the test section from noise from the environment thereby preventing such noise from influencing the measurement of acoustic properties of the fluid 18 in the production tube 16 in the sensing region.

Figure 5:
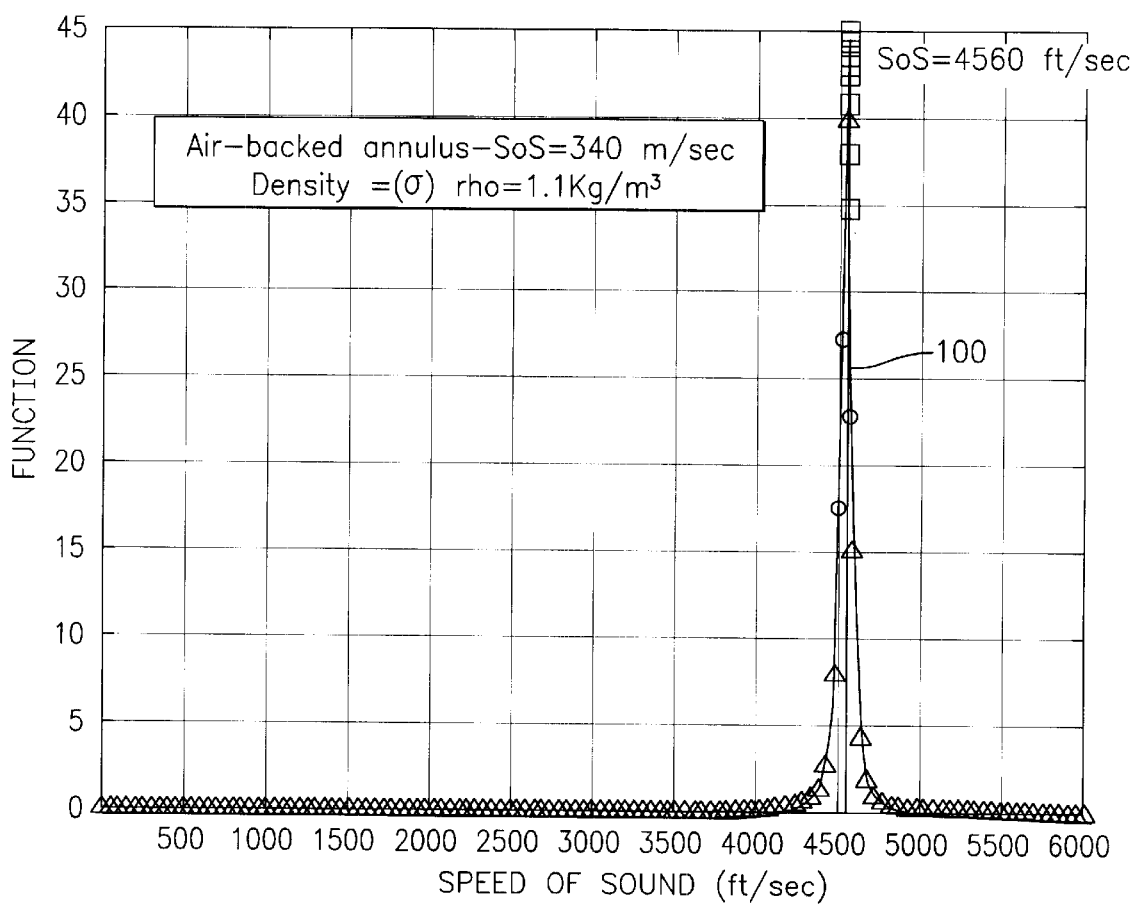
FIG. 5 is a graph that illustrates the speed of sound with an air-backed annulus, in accordance with the present invention.

Referring to FIG. 5, a plot of a simulation curve 100 where water is the fluid 18 contained in the production tubing 16 and the cavity 32 is filled with air (or is air-backed) at a pressure of 1 atm (or 14.7 psi) having a speed of sound=340 meters/sec and a density $\rho=1.1$ kg/m$^3$. The production tube 16 is a steel tube having a diameter of 3.0 inches, and the wall thickness of 0.22 inches. The sound speed of water in an infinite media is 4892 ft/sec with a density $\rho w$ of 1000 kg/m$^3$. The curve 100 was calculated from a phased array of strain sensors on the pipe 16, similar to the techniques described in the aforementioned copending patent application. The measured sound speed from the simulation indicates a value of 4560 ft/sec, which can be corrected for pipe thickness as discussed hereinbefore, to determine the infinite media sound speed of water.

Figure 6:
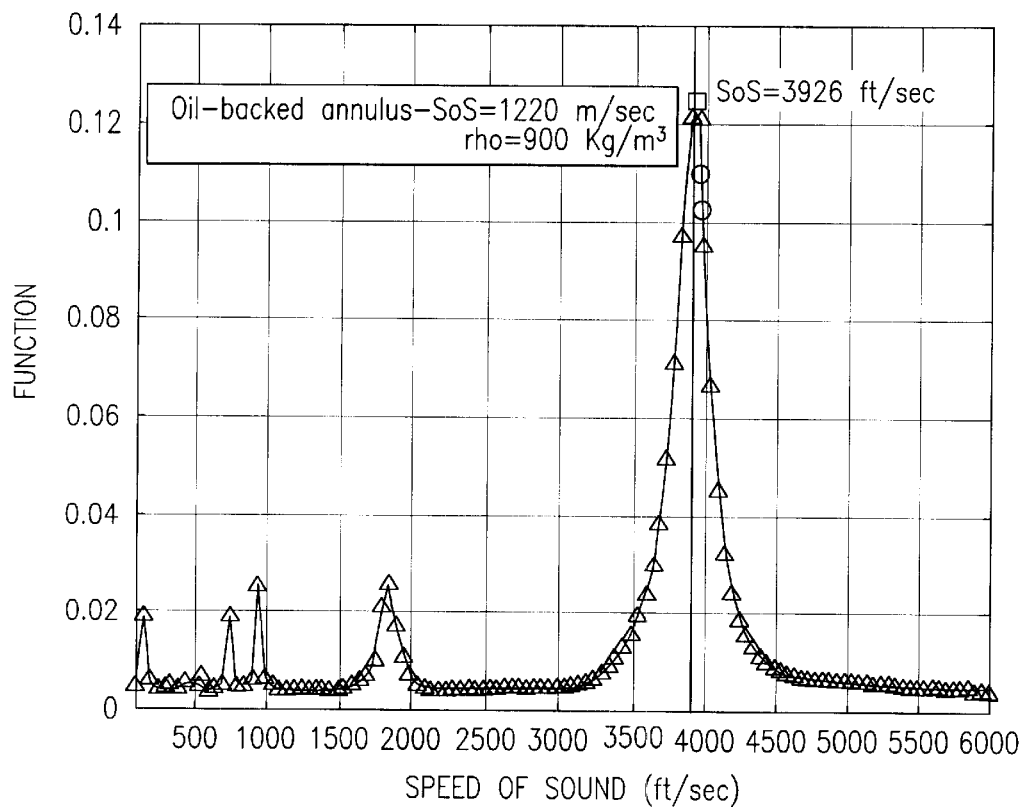
FIG. 6 is a graph that illustrates the speed of sound with an oil-backed annulus, in accordance with the present invention.
Figure 7:
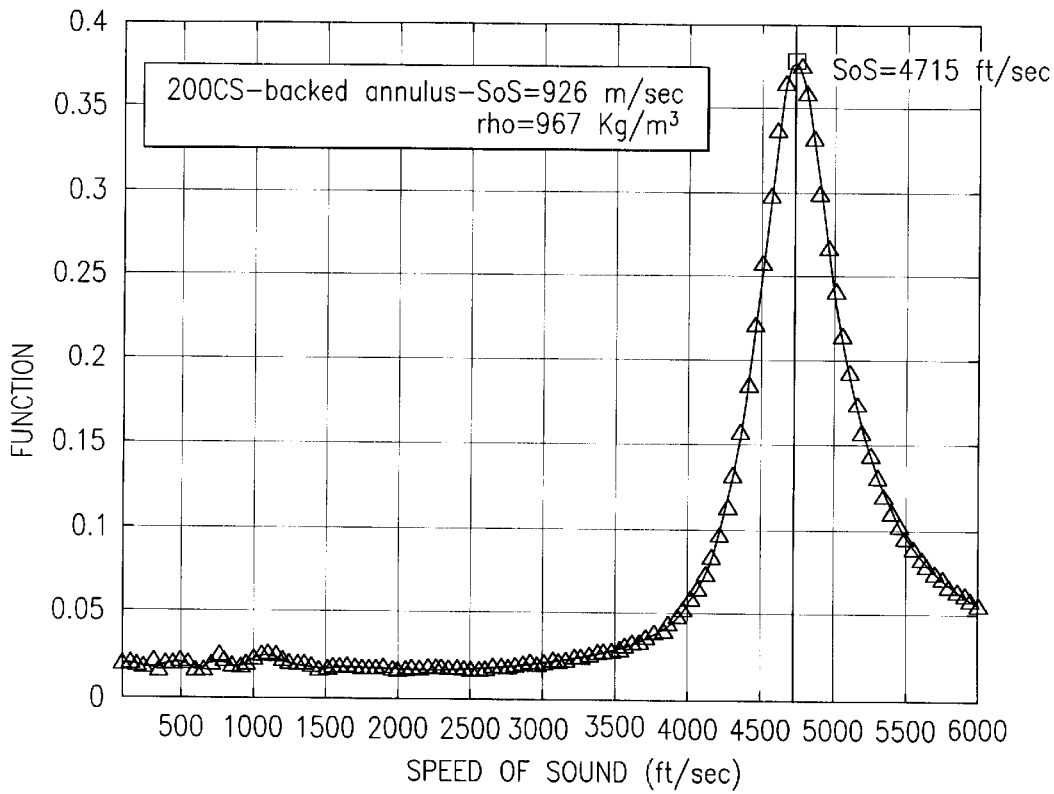
FIG. 7 is a graph that illustrates the speed of sound with an alternative oil-backed annulus, in accordance with the present invention.

Referring to FIGS. 6 and 7, if the cavity 31 is filled with a liquid with acoustic properties similar to water or oil instead of air, the results are much different. Referring to FIG. 6, when the cavity 32 is filled with an oil having a speed of sound=1220 m/sec. and a density $\rho=900$ kg/m$^3$, the measured speed of sound is a value of 3926 ft/sec. Referring to FIG. 7, when the cavity 32 is filled with an oil having a speed of sound=926 m/sec. and a density $\rho=967$ kg/m$^3$, the measured speed of sound is a value of 4715 ft/sec. Without access to a precise model of all the relevant physical parameters external to the pipe 16 in the sensing areas in the oil-backed cases, it would not be possible to accurately determine the sound speed of the produced fluid 18.

It should be understood that strain-based measurements are more sensitive to acoustic isolation than ported pressure measurements. FIGS. 5–7 were generated using unsteady pressures measured using strain sensors on the pipe 16 with the cavity having a length of 54 inches long and an inner diameter of 4.5 inches. The outer shell of the sleeve 30 was modeled as an infinitely rigid containment vessel.

The axial edges of the sleeve may be perpendicular to the cylindrical walls or tapered at a predetermined angle or geometry if desired. Also, the sensors may be connected to a transmission cable (not shown) which may be fed through a wall of the sleeve 30 using a hermetic feed-through. Also, the sleeve may be part of a longer outer sleeve that is attached to the pipe at opposite ends of the sensing section of the pipe 16 (i.e., the axial length of the pipe 16 where the pressure sensors 20–24 are located).

It should be understood that any of the features, characteristics, alternatives or modifications described regarding a particular embodiment herein may also be applied, used, or incorporated with any other embodiment described herein.

Although the invention has been described and illustrated with respect to exemplary embodiments thereof, the foregoing and various other additions and omissions may be made therein and thereto without departing from the spirit and scope of the present invention.

What is claimed is:

1. An apparatus for detecting acoustic pressures in a pipe, said pipe having at least two acoustic sensors that sense acoustic pressures of a produced fluid in said pipe along a sensing section, comprising:
   a closed cavity formed on the outside of said pipe along said sensing section of said pipe and thereby isolating said sensing section from an outside environment; and said acoustic sensors enclosed within said cavity.

2. The apparatus of claim 1 wherein said cavity is filled with a cavity material having an acoustic impedance ($\rho c2$) that is much less than the acoustic impedance ($\rho c1$) of the produced fluid.

3. The apparatus of claim 1 wherein the produced fluid is a liquid and said cavity is filled with a gas.

4. The apparatus of claim 1 wherein the cavity is filled with an inert gas.

5. The apparatus of claim 1 wherein said cavity is filled with air and the produced fluid comprises oil.

6. The apparatus of claim 1 wherein said cavity is evacuated.

7. The apparatus of claim 1 wherein the pressure sensors measure strain on the pipe.

8. The apparatus of claim 1 wherein the geometry of said sleeve is a cylinder.

9. The apparatus of claim 1 wherein said sleeve is connected to said pipe at opposite ends of said sleeve.

10. The apparatus of claim 1 wherein said cavity is formed by an annular sleeve positioned over said pipe along said sensing section.

11. A method for acoustically isolating at least two acoustic sensors that sense acoustic pressures of a produced fluid in a pipe along a sensing section, said method comprising:
    attaching an outer sleeve to the pipe at opposite axial ends of the sensing section, said sleeve forming a closed cavity between said sleeve and said pipe and isolating said sensing section from an environment; and
    enclosing said sensors within said cavity.

12. The method of claim 11 wherein said cavity is filled with a cavity material having an acoustic impedance ($\rho c2$) that is much less than the acoustic impedance ($\rho c1$) of the produced fluid.

13. The method of claim 11 further comprising filling said cavity with a cavity material having an acoustic impedance ($\rho c2$) that is much less than the acoustic impedance ($\rho c1$) of the produced fluid.

14. The method of claim 11 wherein said cavity is filled with a gas and the produced fluid is a liquid.

15. The method of claim 11 wherein said cavity is filled with an inert gas.

16. The method of claim 11 wherein said cavity is filled with air and the produced fluid comprises oil.

17. The method of claim 11 wherein said cavity is evacuated.

18. The method of claim 11 wherein the pressure sensors measure strain on the pipe.

19. The method of claim 11 wherein the geometry of said sleeve is a cylinder.

20. The method of claim 11 wherein the produced fluid is a liquid and further comprising filling said cavity with a gas.

21. The method of claim 11 wherein said cavity is filled with a low impedance gas.

22. The apparatus of claim 2 wherein said annular sleeve includes axial edges and wherein said axial edges are sealed to said pipe thereby forming said closed cavity.

* * * * *